United States Patent [19]

Gelbin et al.

[11] Patent Number: 5,688,847
[45] Date of Patent: Nov. 18, 1997

[54] POLYCYCLIC FLUOROPHOSPHITES USEFUL AS STABILIZERS

[75] Inventors: Michael E. Gelbin, Fords; Michael H. Fisch, East Wayne; R. David Peveler, Woodcliff Lake, all of N.J.

[73] Assignee: Witco Corporation, Greenwich, Conn.

[21] Appl. No.: 745,010

[22] Filed: Nov. 7, 1996

[51] Int. Cl.$^6$ .......................... C07K 5/51; C07F 9/6574
[52] U.S. Cl. ...................... 524/118; 558/74; 558/77
[58] Field of Search ........................ 524/118; 558/74, 558/77

[56] References Cited

U.S. PATENT DOCUMENTS 4,912,155  3/1990  Burton ............................... 524/118
5,061,818  10/1991  Burton et al. ......................... 558/84

*Primary Examiner*—Michael G. Ambrose
*Attorney, Agent, or Firm*—Scully, Scott, Murphy & Presser

[57] ABSTRACT

Disclosed is a fluorophosphite compound of the formula

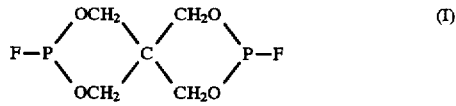

This compound shows superior performance as a stabilizer in polymers, such as polypropylene, and polyvinyl chloride. Also disclosed is a process for making this compound.

15 Claims, No Drawings

POLYCYCLIC FLUOROPHOSPHITES USEFUL AS STABILIZERS

FIELD OF THE INVENTION

The present invention relates to a novel fluorophosphite compound useful as a stabilizer in organic materials such as organic polymers.

BACKGROUND OF THE INVENTION

Phosphites and other organic phosphorus compounds are used as antioxidants and stabilizers in organic materials such as organic polymers. In organic polymers such as polyolefin homopolymers and copolymers, they are generally considered better than phenolic antioxidants at elevated temperatures due to their ability to remove hydroperoxides which decompose and lead to autoxidation chain reactions. Thus, organic phosphorus compounds are important for oxidative stability during numerous operations such as polyolefin extrusion. Additionally, in organic polymers such as polyvinyl chloride organic phosphites are used to improve resistance of the resin to discoloration on exposure to the action of heat or light.

Thus, additives of organic phosphite type are needed in larger amounts for processing organic polymers. Many of the antioxidants and stabilizers employed in organic materials have limited effectiveness or impart undesirable properties such as discoloration. Consequently, there exists a need for novel organic phosphites with improved antioxidant and stabilizing properties. The polycyclic fluorophosphite of the present invention allows organic materials to maintain excellent color and thermal stability.

There have been disclosures in the prior art of fluorophosphites said to be effective to alleviate the shortcomings of organic phosphites such as alkyl aryl phosphites. Examples include U.S. Pat. No. 4,912,155, U.S. Pat. No. 5,061,818 and U.S. Pat. No. 4,962,144. However, there remains a need in this field for fluorophosphite stabilizers for polyolefins and polyvinyl chloride, which exhibit improved stabilization, exemplified by improvements in melt flow and in yellowing index, compared to existing stabilizers and even to existing fluorophosphite stabilizers.

There also remains a need in this field for improvements in processes for synthesizing fluorophosphites.

BRIEF SUMMARY OF THE INVENTION

One aspect of the present invention is the discovery that a compound of the formula

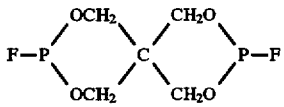

exhibits surprisingly improved effectiveness as a stabilizer as measured by several tests of its performance in formulations with polypropylene and polyvinyl chloride. Another aspect of the present invention is a process for producing the aforementioned compound by reacting pentaerythritol with a phosphorus trihalide, i.e. phosphorus trichloride, phosphorus tribromide or phosphorus triiodide, to form the corresponding dihalo intermediate, and then reacting the intermediate with a suitable fluorinating agent to form the aforementioned fluorophosphite compound (I) by transhalogenation, i.e. exchanging halogen bonded directly to phosphorus with a fluorine atom. Yet another aspect of the present invention is the discovery that this two-step process can be carried out without requiring isolation of the intermediate product, particularly if the reaction is carried out in the presence of any of several suitable amine catalysts.

DETAILED DESCRIPTION OF THE INVENTION

The compound of the formula (I) can also be referred to as 3,9-difluoro-2,4,8,10-tetraoxa-3,9-diphosphaspiro[5.5] undecane. This compound can conveniently be prepared from pentaerythritol via the following synthetic route. First, the pentaerythritol is reacted with any of the aforementioned phosphorus trihalides, e.g. (preferably) phosphorus trichloride. The reaction is preferably carried out in an inert solvent such as toluene, by providing at least the two moles of phosphorus trihalide per mole of pentaerythritol present as required by the stoichiometry of the reaction. Other liquid reaction media useful in carrying out this reaction include inert aprotic solvents such as tetrahydrofuran, benzene, xylene, heptane, octane, cyclohexane, and the like. The reaction is preferably carried out at moderately elevated temperature on the order of 20° C. to 300° C. The preferred reaction temperature is 55° to 70° C.

This reaction is preferably carried out in the presence of a small but effective amount of one or more amine catalysts for the reaction. The preferred amine catalyst is dimethyl formamide. Other amine catalysts include trialkyl amines, such as triethylamine; 1,5-diazabicyclo[4.3.0]non-5-ene; and 1,8-diazabicyclo[5.4.0]undec-7-ene. Mixtures of two or more catalysts can also be employed. A preferred mixture is dimethylformamide and triethylamine, in a volume ratio of dimethylformamide:triethylamine of at least 1:10. Effective amounts of the amine catalyst component generally comprise less than one weight percent of the pentaerythritol.

The progress of this first step can be monitored by assaying the reaction mixture periodically for pentaerythritol or for the phosphorus trihalide.

This first reaction step forms an intermediate chlorinated product of the formula (II)

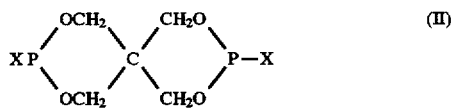

wherein X is Cl, Br or I.

In the second step of the desired reaction, this intermediate (II) is reacted with a fluorinating agent to substitute fluorine for the two halogen atoms in the intermediate of formula (II). Preferred fluorinating agents include ammonium fluoride, $NH_4F$, and antimony trifluoride, $SbF_3$. Other useful fluorinating agents include any fluoride salt capable of transhalogenating phosphorus bound chlorine, bromine, or iodine such as LiF, NaF, KF, RbF, $CaF_2$, CsF, $KHF_2$, AgF, $SnF_4$, and $N(C_2H_5)_3x3HF$, and the like.

The amount of the fluorinating agent added to the reaction mixture should be at least the stoichiometric amount required by the fluorination reaction based on the amount of compound (II) present. This transhalogenation reaction is also carried out in an inert aprotic solvent, a preferred example of which is toluene. Useful temperatures are in the range of 20° C. to 300° C., more preferably from about 50° C. to about 200° C. and most preferably at the atmospheric reflux temperature of the reaction mixture.

The transhalogenation reaction is also preferably catalyzed by an amine transhalogenation catalyst. Many of the amine catalysts useful in the first step of the process of the present invention are also effective in the second step, although triethylamine alone is not. It is a preferred embodiment of this invention to use dimethylformamide catalyst alone or in admixture with certain tertiary amine catalysts that—while commonly catalyzing the first step of the reaction—are known to lack catalytic activity in the transhalogenation step, such as triethylamine.

Thus, it is preferred, and is one of the useful aspects of the process of the present invention, that the two reaction steps (i.e. the formation of the bicyclo halogenated intermediate (II), and the fluorination of this intermediate) can be carried out in sequence, and even in the same reaction vessel, without the need to isolate the bicyclo halogenated intermediate (II) from its reaction mixture. Thus, the solvent and the amine catalyst added in the course of the first reaction step remain present for the second reaction step.

The progress of the second step in the reaction can be monitored by assaying the reaction mixture for the amount of the halogenated intermediate (II) present. If necessary, additional fluorinating agent can be added during the course of the reaction to promote complete conversion of the intermediate (II) to the desired final fluorophosphite product.

When the reaction to form the fluorophosphite product (I) has proceeded to completion, the reaction mixture is preferably filtered to remove solids, and the product (I) can be recovered from the filtrate after removing the solvent.

Typically, the aforementioned reaction steps also simultaneously produce a structural isomer of the formula

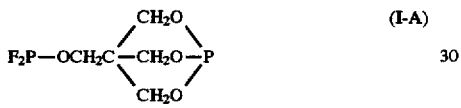

(I-A)

This isomer can be separated from the bicyclo compound of formula (I), but need not be separated therefrom. The synthetic procedures described herein generally produce products of formulas (I) and (I-A) in ratios on the order of 95:5 (I:I-A). Carrying out the reactions at higher temperature increases the amount of the isomer of formula (I-A) relative to that of formula (I). Thus, the present invention is considered to embrace the compounds of formulas (I) and (I-A) as well as mixtures of said compounds.

The products of the present invention are useful as stabilizers for polymer compositions including polypropylene and vinyl halide resins, preferably polyvinyl chloride resins. Stabilization is provided against discoloration over time and against discoloration upon exposure to heat such as the elevated temperatures encountered in processing operations such as extrusion and molding.

The term "polyvinyl chloride" as used herein is inclusive of any polymer formed at least in part of the recurring group (—CH$_2$CXCl—)$_p$ and having a chlorine content in excess of 40%. In this formula, the X group can be either hydrogen or chlorine, and p is the number of units in each polymer chain. In polyvinyl chloride homopolymers, the X group is hydrogen, whereas in polyvinylidene chloride X is Cl. Thus, the terms "PVC" and "polyvinyl chloride" include not only polyvinyl chloride homopolymers but also after-chlorinated polyvinyl chlorides, as well as copolymers of vinyl chloride in a major proportion such as copolymers of vinyl chloride and vinyl acetate, copolymers of vinyl chloride with maleic or fumeric acids or esters, and copolymers of vinyl chloride with styrene. Also included are mixtures of polyvinyl chloride in major proportion with a minor proportion of other synthetic resins such as chlorinated polyethylene or copolymers of acrylonitrile, butylene and styrene.

The synthesis of the product of formula (I) of the present invention is described in the following Examples 1 and 2.

EXAMPLE 1

A dry 300 mL three-necked round bottomed flask was fitted with stirrer, condenser and addition funnel. The condenser was connected to an HCl scrubber. Then 27.2 g (200 mmol) of pentaerythritol, 60 mL of dry toluene and a mixture of 1 mL triethylamine and 0.1 mL dimethylformamide was added. With stirring 54.8 g (400 mmol) phosphorus trichloride (PCl$_3$) was added dropwise at room temperature over a period of 20 min. While vigorous gas evolution began, the temperature was gradually raised to 55° C. over a period of 3 h. Toward the end of the effervescent reaction, the mixture was protected with a nitrogen blanket. A suspension of 23.7 g (133 mmol) antimony trifluoride (SbF$_3$) in 10 mL toluene was then quickly added with stirring. The mixture was then kept with stirring at 55° C. A $^{31}$P-NMR sample taken after 1.5 h showed 23% unreacted product of formula (II). Hence further 2.5 g SbF$_3$ was added. A $^{31}$P-NMR sample taken after another 30 min. showed no more signal for product of formula (II), indicating full conversion. The $^{31}$P-NMR yield for the product of formula (I) at that point was 89%. Subsequently, 0.5 g filter aid was added to the cooled mixture which was filtered. Toluene was removed from the clear filtrate by vacuum distillation through a short Vigreux column. The column was removed and the oily residue distilled in vacuo. A fraction distilling at 0.5 mm/75°–78° C. was collected. Yield: 31 g (66% rel. to pentaerythritol).

EXAMPLE 2

To an oven-dried 100 mL three-necked round bottomed flask equipped with stirrer, condenser and addition funnel was added 20.5 g (150 mmol) of pentaerythritol, 20 mL of dry toluene and 0.1 mL of 1,8-diazabicyclo[5.4.0]undec-7-ene. While stirring 43.3 g (315 mmol) phosphorus trichloride was added dropwise at room temperature over a period of 10 min. While vigorous gas evolution began, the temperature was gradually raised to 70° C. over a period of 3 h and kept with stirring for an extra 2 h. Then 11.7 g (315 mmol) ammonium fluoride (NH$_4$F) was added. The mixture was heated to reflux. After 2 h, a further 2.5 g of NH$_4$F was added. A $^{31}$P-NMR sample taken after 1 hr of further refluxing showed no more signal for product of formula (II), indicating full conversion. Subsequently, the cooled mixture was filtered. Toluene was removed from the clear filtrate in vacuo. 22.7 g (64% rel. to pentaerythritol) of material was collected which solidified upon standing.

The following examples show the performance of the bicyclic fluorophosphite of formula (I) as a stabilizer in polypropylene and polyvinyl chloride. It also presents the performance of this compound in comparison to other stabilizers, including other fluorophosphite stabilizers. The data show that the fluorophosphite stabilizer of the present invention shown in formula (I) is superior to the other fluorophosphites, by a significant degree, and is comparable to or superior to other stabilizers used for the same purpose.

EXAMPLE 3

Process Stabilization of Polypropylene at 475° F.

This example illustrates the stabilizing effectiveness of the bicyclic fluorophosphite of the present invention in combination with a representative phenolic antioxidant, in polypropylene as compared to other representative prior art compounds and other fluorophosphites.

The base formulation comprised unstabilized polypropylene (PROFAX® 6501, Hercules Chemical) containing 0.1% by weight of tetrakis[methylene{3,5-di-tert-butyl-4-hydroxycinnamate}]methane as phenolic antioxidant. The test additives, at 0.2% by weight, were incorporated into polypropylene by dry blending or, when the additive was a liquid, using a minimum amount of heptane solvent, following which the solvent was removed by evaporating under reduced pressure. The stabilized resin formulation was extruded at 50 rpm form a 1 inch diameter extruder (Killion single-screw) at 475° F.

After each of the 1st, 3rd and 5th extrusion, resin pellets obtained were compression molded into 60 mil thick plaques at 450° F., and specimen yellowness index (YI) determined on a Hunterlab Optical Sensor. Lower YI values indicate less discoloration.

After each of the first, third and fifth extrusion, the melt flow rate (in g/10 min.) was also determined by ASTM method D 1238 condition L on the pellets obtained from the extruder, using a Titanium Olson Extrusion Plastometer.

The results are shown in Table 2.

TABLE 1

The fluorophosphites which were tested and for which results are given in Table 2, are coded as follows:

| Code | Description |
|---|---|
| FP-1 | 3,9-difluoro-2,5,8,10-tetraoxa-3,9-diphosphaspiro[5.5]undecane (product of the present invention) |
| FP-2 | bis(2,6-di-sec-butylphenyl)fluorophosphite |
| FP-3 | FP-2 (85%), Bis(2,6-di-sec-butylphenyl)chlorophosphite (7%), and FP'-2(8%)* |
| FP-4 | bis(6-tert-butyl-2,4-dimethylphenyl)fluorophosphite |
| FP-5 | bis(2,4-di-tert-butyl-6-methylphenyl)fluorophosphite |

*$^{31}$P-NMR percent

These results show that the fluorophosphite of the present invention protects polypropylene from discoloration far better than phenolic antioxidant alone or than does prior art stabilizer.

TABLE 2

| | Extrusion #1 | | Extrusion #3 | | Extrusion #5 | |
|---|---|---|---|---|---|---|
| Additive | Flow Rate g/10 min | Yellowness Index | Flow Rate g/10 min | Yellowness Index | Flow Rate g/10 | Yellowness Index |
| Base | 5.9 | 4.7 | 8.8 | 5.8 | 9.7 | 6.3 |
| Base + PS-1 | 3.7 | 6.6 | 4.1 | 9.0 | 4.5 | 11.3 |
| Bass + PS-2 | 3.9 | 9.1 | 4.3 | 10.9 | 5.0 | 12.0 |
| Base + FP-1 | 5.0 | 2.6 | 6.1 | 3.2 | 6.8 | 4.7 |
| Base + FP-2 | 3.3 | 4.7 | 3.9 | 6.1 | 4.6 | 7.1 |
| Base + FP-3 | 3.5 | 4.5 | 3.7 | 5.5 | 4.7 | 6.6 |
| Base + FP-4 | 2.5 | 3.9 | 3.1 | 4.4 | 3.2 | 5.1 |
| Base + FP-5 | 2.8 | 5.3 | 3.3 | 6.2 | 3.7 | 7.7 |

PS-1: Tris(2,4-di-tert-butylphenyl)phosphite
PS-2: 2,2'-Ethylidene bis (4,6-di-tert-butylphenyl) fluorophosphite The formulations containing product FP-1, the product of the present invention, consistently exhibited significantly greater stabilization against discoloration (seen as a significantly lower yellowness index) compared to formulations containing other additives.

EXAMPLE 4

Process Stabilization of Polyvinyl Chloride

This example illustrates the stabilizing effectiveness of the bicyclic fluorophosphite of the present invention in polyvinyl chloride. Thus, 100 parts by weight of polyvinyl chloride Oxy 225, 50 parts by weight of diisodecyl phthalate, five parts by weight of epoxidized soybean oil Drapex 6.8, 0.2 parts by weight of stearic acid, and two parts by weight of barium/zinc stabilizer Mark 6705 were throughly mixed with 0.5 parts by weight of FP-1 and then homogenized by working on a roll mill heated at 160° C. The composition thus produced was removed in the form of a colorless sheet.

This sheet proved resistant to color changes upon being subjected to 178° C. for 105 min. A first control without FP-1 seriously discolored under these conditions. A second control with a representative phosphite stabilizer, octyl diphenyl phosphite, in place of FP-1, used at one part by weight, displayed serious discoloration under these conditions, as well.

What is claimed is:

1. A compound of the formula (I)

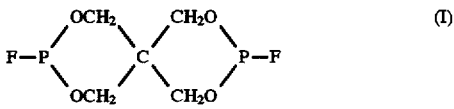

2. A product selected from the group consisting of

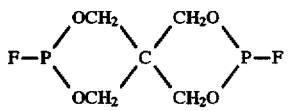

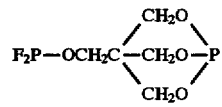

and (c) mixtures of (a) and (b).

3. A process for producing a compound of the formula (I)

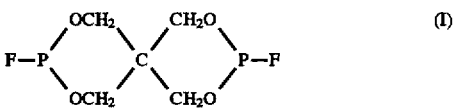

comprising (a) reacting pentaerythritol with $PX_3$ to form a compound of the formula (II)

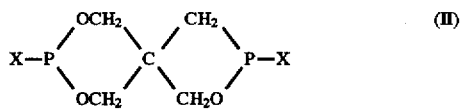

wherein X is Cl, Br or I, and (b) reacting the compound of formula (II) with a fluorinating agent to form said compound of formula (I).

4. A process according to claim 3 wherein step (b) is carried out without isolating said compound of formula (II) from the reaction product formed in step (a).

5. A process according to claim 3 wherein the reaction of step (a) is carried out in the presence of an organoamine catalyst.

6. A process according to claim 5 wherein said catalyst comprises dimethylformamide.

7. A process according to claim 5 wherein said catalyst is a mixture of dimethylformamide and triethylamine.

8. A process according to claim 5 wherein said catalyst comprises 1,8-diazabicyclo[5.4.0]undec-7-ene.

9. A process according to claim 5 wherein X is Cl.

10. A process according to claim 3 wherein said fluorinating agent is selected from the group consisting of $NH_4F$, $SbF_3$, LiF, NaF, KF, RbF, $CaF_2$, $KHF_2$, AgF, $SnF_4$, $N(C_2H_5)_3$ x3HF, and mixtures thereof.

11. A composition of matter comprising a polymer selected from the group consisting of polyvinyl chlorides and polyolefins, and the compound of claim 1 in a minor amount effective to stabilize said polymer.

12. A composition according to claim 11 wherein the amount of said stabilizer is up to 0.25% by weight of the polymer.

13. A composition according to claim 11 wherein said polymer is polypropylene.

14. A composition according to claim 11 wherein said polymer is polyethylene.

15. A composition according to claim 11 wherein said polymer is polyvinyl chloride.

* * * * *

UNITED STATES PATENT AND TRADEMARK OFFICE
CERTIFICATE OF CORRECTION

PATENT NO. : 5,688,847
DATED : November 18, 1997
INVENTOR(S) : Michael E. Gelbin, et al.

It is certified that error appears in the above-indentified patent and that said Letters Patent is hereby corrected as shown below:

Column 5, line 55: "Bass" should read --Base--

Signed and Sealed this

Second Day of February, 1999

Attest:

Attesting Officer

*Acting Commissioner of Patents and Trademarks*